United States Patent [19]

Hanayama et al.

[11] Patent Number: 5,077,424

[45] Date of Patent: Dec. 31, 1991

[54] PHOSPHITE COMPOUNDS

[75] Inventors: Naoki Hanayama, Suzuka; Kazuo Nakagawa; Akiyoshi Onishi, both of Yokkaichi, all of Japan

[73] Assignees: Yoshitomi Pharmaceutical Industries, Ltd., Osaka; Mitsubishi Petrochemical Company, Ltd., Tokyo, both of Japan

[21] Appl. No.: 326,038

[22] Filed: Mar. 17, 1989

[30] Foreign Application Priority Data

Mar. 29, 1988 [JP] Japan .................................. 63-77622

[51] Int. Cl.$^5$ ............................................ C07F 9/145
[52] U.S. Cl. ........................................................ 558/198
[58] Field of Search ........................................ 558/198

[56] References Cited

U.S. PATENT DOCUMENTS

| | | | |
|---|---|---|---|
| 3,558,554 | 1/1971 | Kuriyama | 558/218 |
| 4,163,007 | 7/1979 | Lind et al. | 558/198 |
| 4,182,704 | 1/1980 | Spivack | 558/198 |
| 4,187,212 | 2/1980 | Zinke | 558/218 |

FOREIGN PATENT DOCUMENTS

| | | |
|---|---|---|
| 3301641 | 4/1956 | Japan . |
| 3712373 | 4/1960 | Japan . |
| 1580914 | 12/1980 | United Kingdom . |

OTHER PUBLICATIONS

Derwent Accession No. 84-045041/08.
Chemical Abstracts, 100(24), 193021x.

*Primary Examiner*—Mary C. Lee
*Assistant Examiner*—Michael G. Ambrose
*Attorney, Agent, or Firm*—Wenderoth, Lind & Ponack

[57] ABSTRACT

Phosphite compounds represented by the formula

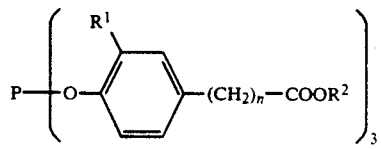

wherein $R^1$ stands for a tertiary hydrocarbyl group, $R^2$ stands for an alkyl group, an aralkyl group which may be substituted, an aryl group or a cycloalkyl group and n stands for 0, 1 or 2.

Such compounds possess stabilizing action against organic materials, particularly antioxidant action, and are useful as antioxidants for preventing deterioration by oxidation of organic materials.

2 Claims, 1 Drawing Sheet

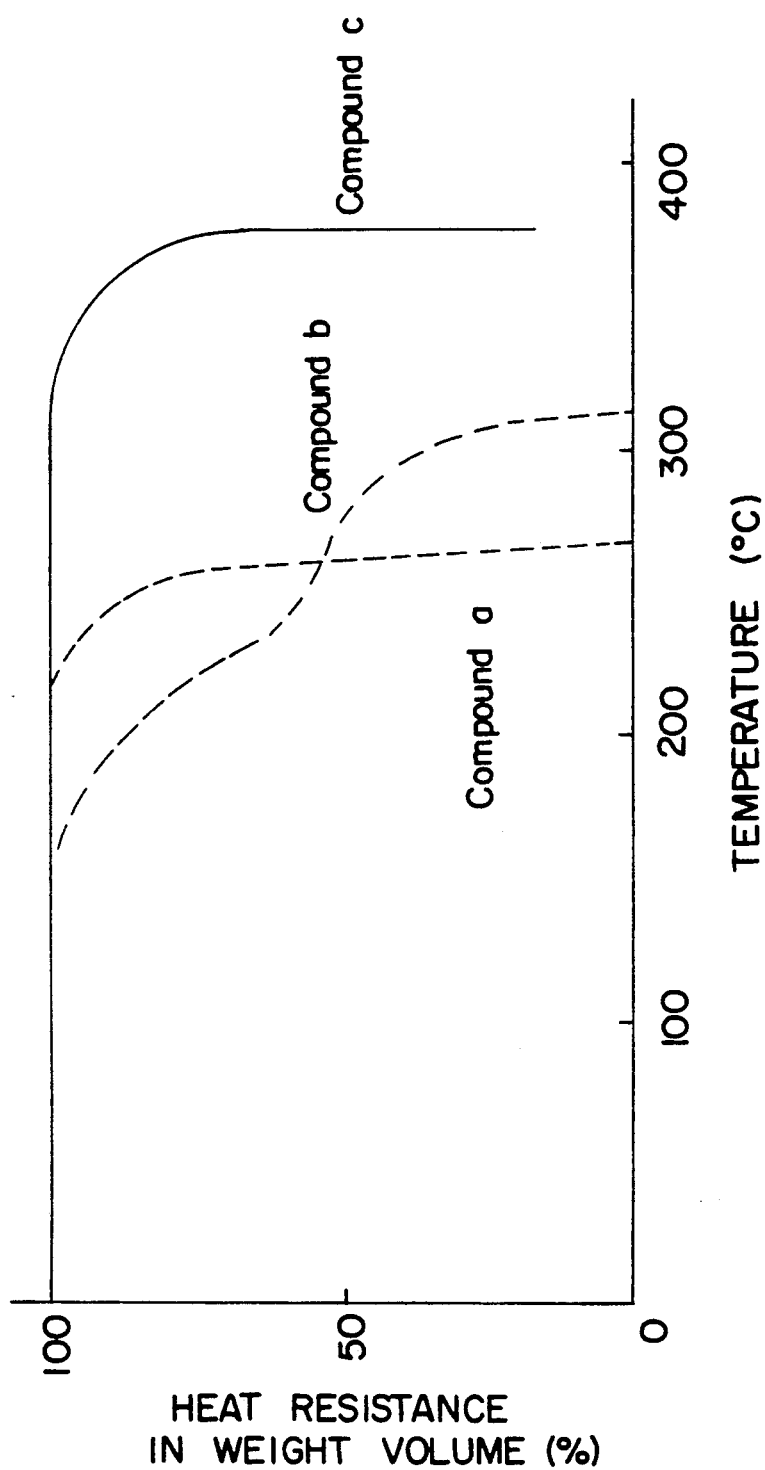

PHOSPHITE COMPOUNDS

BACKGROUND OF THE INVENTION

This invention relates to novel phosphite compounds which are useful as stabilizing agents for organic materials. Since organic materials which consist of natural macromolecules, synthetic macromolecules, fats and oils, lubricants, working oils or so on are subject to oxidation and decrease in utility, various antioxidants have been devised and have been added to these organic materials. It is known that stabilizers such as hindered phenols, organic sulfur compounds, organic phosphorus compounds and aromatic amines have stabilizing effects when used singly or in combination. The above-mentioned stabilizing agents have their respective merits and are useful. In particular, phosphite compounds of organic phosphorus compounds are widely used as antioxidants.

As concrete examples of phosphite compounds, there have been known the compounds which are described in the gazettes of Japanese Patent Application Examined Publication (Kokoku) No. 1641/1958 and Japanese Patent Application Unexamined Publication (Kokai) No. 4629/1984.

As concrete examples of attempt for stabilizing effects with the combined use of phosphite compounds and hindered phenol compounds, there have been such combined use in the gazette of Japanese Patent Application Examined Publication No. 12373/1962 in the specification of U.S. Pat. No. 3,558,554, in the gazette Japanese Patent Publication Application Unexamined Publication No. 109050/1976 and in the gazette of Japanese Patent Application Examination Publication No. 21822/1987.

However, the above-mentioned phosphite compounds hitherto known include various problems, and satisfactory phosphite compounds are thus far unknown.

Specifically, the above-mentioned known phosphite compounds have problems which include, among others, the problem that since the phosphite compounds are susceptible to hydrolysis and thermal decomposition, sufficient stabilizing effect cannot be realized and inconveniences such as corrosion and foul-smell are apt to occur. Phosphite compounds having sterically bulky structure in the neighborhood of the phosphite bond involve the problem that they are difficult to synthesize. For example, in the case where tris(2,4,6-trisubstituted phenyl)phosphites have a bulky group such as tert-butyl group as the substituents at the 2- and 6- positions, they are difficult to synthesize and are industrially less valuable.

SUMMARY OF THE INVENTION

Accordingly, the object of the present invention is to provide phosphite compounds which are easy to synthesize, scarcely decompose and exhibit high stabilizing effects.

Another object of the present invention is to provide stabilizing agents for organic materials comprising the novel phosphite compounds.

A further object of the present invention is to provide stabilized organic materials comprising the novel phosphite compounds in combination with, if desired, hindered phenol compounds, thioalkanoate compounds or light stabilizing agents.

BRIEF DESCRIPTION OF THE DRAWING

FIG. 1 is a graph depicting the heat resistance of compounds of the present invention vs. temperature.

DETAILED DESCRIPTION

Said object can be attained according to the present invention, that is, the phosphite compound represented by the formula

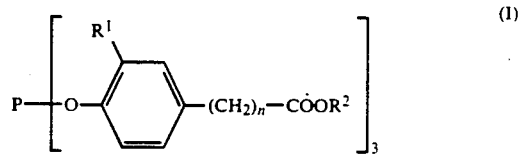

wherein $R^1$ stands for a tertiary hydrocarbyl group, $R^2$ stands for an alkyl group, an aralkyl group which may be substituted, an aryl group or a cycloalkyl group and n stands for 0, 1 or 2 [hereinafter referred to as compound (I)].

In the above-mentioned definition, the tertiary hydrocarbyl group includes, for example, hydrocarbyl groups having not less than 4 carbon atoms, namely, tertiary alkyls, tertiary aralkyls, tertiary aryls, tertiary cycloalkyls and so on.

Among them, preferred are alkyl groups and cycloalkyls having 4 to 10 carbon atoms, which are exemplified by, particularly, tertiary butyl group, the tertiary pentyl group, 1,1,3,3-tetramethylbutyl group, α-methylcyclohexyl group and the like.

As the alkyl groups, mention is made of straight- or branched-alkyl groups having 1 to 22 carbon atoms such as methyl, ethyl, propyl, isopropyl, butyl, isobutyl, sec-butyl, tert-butyl, pentyl, isopentyl, neopentyl, tert-pentyl, hexyl, isohexyl, 1-methylpentyl, heptyl, octyl, 2-ethylhexyl, 1,1,3,3-tetramethylbutyl, nonyl, decyl, undecyl, dodecyl, tridecyl, tetradecyl, pentadecyl, hexadecyl, heptadecyl, octadecyl, nonadecyl, eicocyl, dococyl and the like.

In the aralkyl group which may be substituted, as the aralkyl group, there can be mentioned benzyl, 2-phenylethyl, 3-phenylpropyl, 4-phenylbutyl, 1-naphthylmethyl, 2-naphthylmethyl, 2-(2-naphthyl)ethyl, 2-naphthylmethyl, 2-(2-naphthyl)-ethyl, 4-(2-naphthyl)-butyl and the like. As the substituent, alkyl groups and phenyl group are mentioned. As the alkyl group as the substituent, mention may be made of straight- or branched-alkyl groups having 1 to 4 carbon atoms (e.g. methyl, ethyl, propyl, isopropyl, butyl). The aralkyl groups have 1 to 3 said substituents on the aromatic ring.

In the aryl group which may have substituent(s), as the aryl group, there may be phenyl group and naphthyl group. As the substituent thereof, there are mentioned alkyl groups, phenyl group and the like. As the alkyl group as the substituent, mention is made of straight- and branched-alkyl groups having 1 to 4 carbon atoms (e.g. methyl, ethyl, propyl, isopropyl, butyl). The aryl groups have 1 to 3 said substituents on the aromatic ring.

In the cycloalkyl group which may have substituent(s), as the cycloalkyl group, mention may be made of cyclopropyl, cyclobutyl, cyclopentyl, cyclohexyl, cycloheptyl and the like having 3 to 7 carbon atoms. As the substituent thereof, there may be mentioned alkyl groups, phenyl group and the like. The alkyl groups as the substituent include straight- or branched-alkyl groups having 1 to 3 carbon atoms (e.g. methyl, ethyl, propyl, isopropyl). The alkyl group has 1 to 3 said substituent(s).

The compounds of the formula (I) of the present invention have the following characteristics:

Firstly, it is essentially critical that in the formula (I), the substituent at the 4-position of the phenyl nucleus is not a simple alkyl group such as methyl group, ethyl group, propyl group, butyl group, octyl group, nonyl group or dodecyl, but a group of the formula $-(CH_2)_n-COOR^2$. That is, the structure of the substituent at the 4-position is not particularly restrictive in the synthesis of the compound (I). Besides, the substituent is an important factor to impart necessary properties as a stabilizing agent such as solubility in organic compounds or organic materials to be stabilized, polymerization of the compound (I) and decomposition-resistance.

Secondly, it is significantly meaningful that the compounds (I) have no substituent at the 6-position. That is, the compounds substituted by sterically bulky group such as tert-butyl group at the 6-position, which are difficult to synthesize, are substantially distinguishable from the compounds (I).

The compounds of formula (I) wherein n is 2 are preferable.

As the concrete examples of the compound (I), the following can be mentioned.

Tris[2-tert-butyl-4-(2-(methoxycarbonyl)ethyl)-phenyl]phosphite
Tris[2-tert-butyl-4-(2-(butoxycarbonyl)ethyl)phenyl]-phosphite
Tris[2-tert-butyl-4-(2-(2-ethylhexyloxycarbonyl)ethyl)phenyl]-phosphite
Tris[2-tert-butyl-4-(2-(dodecyloxycarbonyl)ethyl)-phenyl]phosphite
Tris[2-tert-butyl-4-(2-(tridecyloxycarbonyl)ethyl)-phenyl]phosphite
Tris[2-tert-butyl-4-(2-(octadecyloxycarbonyl)ethyl)-phenyl]phosphite
Tris[2-tert-butyl-4-(2-(docycyloxycarbonyl)ethyl)-phenyl]phosphite
Tris[2-tert-butyl-4-(2-(phenoxycarbonyl)ethyl)-phenyl]phosphite
Tris[2-tert-butyl-4-(2-benzyloxycarbonyl)ethyl)-phenyl]phosphite
Tris[2-tert-butyl-4-(2-(phenoxycarbonyl)ethyl)-phenyl]phosphite
Tris[2-tert-butyl-4-(2-(3-methylphenoxycarbonyl)ethyl)phenyl]-phosphite
Tris[2-tert-butyl-4-(2-(4-tert-butylphenoxycarbonyl)ethyl)-phenyl]phosphite
Tris[2-tert-butyl-4-(2-(2,6-dimethylphenoxycarbonyl)ethyl)-phenyl]phosphite
Tris[2-tert-pentyl-4-(2-(octadecyloxycarbonyl)ethyl)phenyl]-phosphite
Tris[2-(1,1,3,3-tetramethylbutyl)-4-(2-(octadecyloxycarbonyl)-ethyl)phenyl]phosphite
Tris[2-(α-methylcyclohexyl)-4-(2-(octadecyloxycarbonyl)-ethyl)phenyl]phosphite The compounds (I) can be produced by reacting the compound of the formula

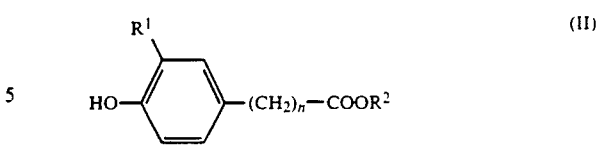

wherein each symbol is of the same meaning as defined above [hereinafter referred to as compound (II)] with the compound of the formula

wherein X stands for a halogen atom [hereinafter referred to as compound (III)] or the compound of the formula

wherein $R^5$ stands for an alkyl or an aryl [hereinafter referred to as compound (IV)].

The reaction of the compound (II) with the compound (III) usually proceeds in a solvent such as benzene, toluene, hexane, heptane, diethyl ether, tetrahydrofuran, chloroform, carbon tetrachloride, dichloroethane, chlorotoluene or chlorobenzene in the presence of an amine such as pyridine, dimethylformamide, triethylamine, dimethylaniline and diethylaniline under cooling or at a temperature ranging from room temperature to the boiling point of the used solvent for 30 minutes to 24 hours. The reaction of the compound (II) with the compound (IV) usually proceeds in the presence of a base such as sodium hydroxide, potassium hydroxide or sodium methoxide in a solvent such as toluene, benzene, hexane, heptane, chlorotoluene or chlorobenzene at a temperature ranging from room temperature to 200° C. for 1 hour to 24 hours.

The obtained objective compound (I) can be purified by a conventional means such as recrystallization, chromatography and the like.

The compound (II) can be produced by reacting the compound of the formula

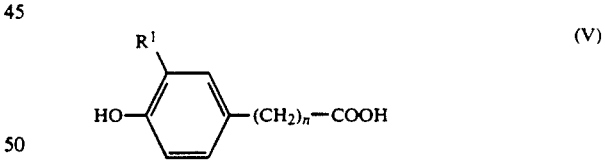

wherein each symbol is of the same definition as mentioned above [hereinafter referred to as compound (V)] with the compound of the formula

wherein $R^2$ is as defined above [hereinafter referred to as compound (VI)] or by subjecting the compound of the formula

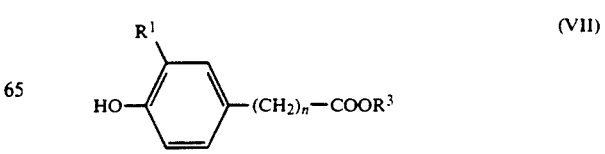

wherein $R^3$ is methyl and $R^1$ and n are as defined above [hereinafter referred to as compound (VII)] which can be obtained by the above-mentioned reaction with the use of the compound of the formula (VI) wherein $R^2$ is methyl or ethyl, with the compound of the formula $$R^4-OH \qquad (VIII)$$

wherein $R^4$ is the same group as $R^2$ excluding methyl and ethyl [hereinafter referred to as compound (VIII)] to ester interchange reaction.

Also, the compound (II) can be produced by conducting elimination reaction for the tert-hydrocarbyl group of the compound of the formula

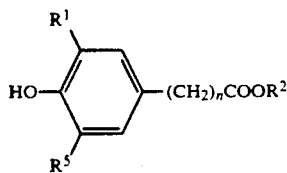

wherein $R^5$ stands for a tert-hydrocarbyl group and the other symbols are as defined above [hereinafter referred to as compound (IX)] in the presence of an acidic substance.

The esterification reaction of the compound (V) with the compound (VI) usually proceeds in the presence of an acid such as hydrochloric acid, sulfuric acid, perchloric acid or p-toluenesulfonic acid, a base such as sodium hydroxide, potassium hydroxide, sodium methoxide, a tin compound such as monobutyltin oxide, dibutyltin oxide, monobutyltin chloride or a phosphorus halide compound such as phosphorus trichloride or phosphorus oxychloride in a solvent such as benzene, toluene, hexane or heptane at a temperature ranging from room temperature to 200° C. for 1 hour to 24 hours.

The ester interchange reaction of the compound (VII) with the compound (VIII) usually proceeds under the same conditions as the above-mentioned esterification reaction As the acidic substance usable for the elimination reaction of the tert-hydrocarbyl group of the compound (IX), there can be mentioned inorganic acids such as sulfuric acid, hydrochloric acid and perchloric acid and organic acids such as trifluoroacetic acid, benzenesulfonic acid and p-toluene-sulfonic acid. The reaction proceeds in a solvent such as dichloroethane, chloroform, benzene or toluene under cooling or at a temperature ranging from room temperature to the boiling point of the used solvent for 30 minutes to 24 hours.

As for the formula (IX), as the tert-hydrocarbyl group represented by $R^5$, mention can be made of the same terthydrocarbyl group as those with regard to the above-mentioned $R^1$.

The compounds (I) of the present invention possess stabilizing action against organic materials, particularly antioxidant action, and are useful as antioxidants for preventing deterioration by oxidation of organic materials.

Organic materials to be stabilized by the compound (I) of the present invention are exemplified by macromolecular polymers, fats and oils, mineral oils themselves and those represented thereby.

As the macromolecular polymers, mention can be made of polyolefin polymers or copolymers thereof such as α-olefin polymers or methylene-vinyl acetate co-polymers and methylenepropylene copolymers exemplified by polyethylene, polypropylene, polybutene, poly-3-methylbutylene, halogen-containing synthetic resins such as poly(vinyl chloride), poly(vinyl fluoride), poly(vinylidene fluoride), poly(brominated ethylene), chlorinated rubber, vinyl chloride-vinyl acetate copolymers, vinyl chloride-methylene copolymers, vinyl chloride-propylene copolymers, vinyl chloride-styrene copolymers, vinyl chloride-isobutylene copolymers, vinyl chloride-vinylidene chloride copolymers, vinyl chloride-styrene-maleic acid anhydride terpolymers, vinyl chloride-styrene-acrylonitrile copolymers, vinyl chloride-butadiene copolymers, vinyl chloride-isobutylene copolymers, vinyl chloride-propylene chloride copolymers, vinyl chloride-isopropylene copolymers, vinyl chloride-vinylidene chloride-vinyl acetate terpolymers, vinyl chloride-acrylate copolymers, vinyl chloride-malerate copolymers, vinyl chloride-methacrylate, vinyl chloride-acrylonitrile copolymers and internal plastic polyvinyl chlorides, petroleum resins, cumarone resins, polystyrenes, poly(vinyl acetate), acryl resins, copolymers of styrene with other monomers (maleic anhydride, butadiene, acrylonitrile and the like), acrylonitrile-butadiene-stylene copolymers, acrylate-butadienestyrene copolymers, methacrylate-butadiene-styrene copolymers, methacrylate resins such as poly(methyl methacrylate), poly(vinyl alcohol), poly(vinyl formal), poly(vinyl butyral), straight-chain polyesters, polyphenyleneoxide, polyamides, polycarbonates, polyacetals, polyurethanes, fiber-resins, unsaturated polyester resins, phenol resins, urea resins, melamine resins, epoxy resins, silicone resins polyethylene terephthalate, polyphenylenesulfide, polybutylene terephthalate, polysulfone resins, polyethersulfone, polyetheretherketone, polyarylate, polyetherimide, polyetherimide, polyimides, maleimide, polyamideimide and the like. Further, there are included rubbers such as natural rubbers, isoprene rubbers, butadiene rubbers, acrylonitrile-butadiene copolymer rubbers and blend of the above-mentioned resins.

In case where the compounds (I) of the present invention are used as stabilizing agents for organic materials, they are used preferably together with hindered phenol compounds.

As the hindered phenol compounds, there may be mentioned 2,6-di-tert-butyl-4-methylphenol, 4-hydroxymethyl-2,6-di-tert-butylphenol, 2,6-di-tert-butyl-4-ethylphenol, butylhydroxyanisole, octadecyl 3-(4-hydroxy-3,5-di-tert-butylphenyl)propionate distearyl (4-hydroxy-3-methyl-5-tert-butyl)benzylmalonate, propyl gallate, octyl gallate, dodecyl gallate, tocopherol, 2,2'-methylenebis(4-ethyl-6-tert-butylphenol), 4,4-methylenebis(2,6-di-tert-butylphenol), 4,4'-butylidenebis(6-tert-butyl-m-cresol), styrene phenol, N,N'-hexamethylenebis(3,5-di-tert-butyl-4-hydroxyhydrocinnamide), 3,5-di-tert-butylhydroxybenzylphosphonic acid aminoethyl ester calcium, 1,1,3-tris(2-methyl-4-hydroxy-5-tert-butylphenyl)butane, 1,3,5-trimethyl-2,4,6-tris(3,5-di-tert-butyl-4-hydroxybenzyl)-benzene, tetrakis[3-(3,5-di-tert-butyl-4-hydroxyphenyl)propionyloxymethyl]methane, 1,6-hexanediol-bis[3-(3,5-ditert-butyl-4-hydroxyphenyl)propionate], 2,2'-dihydroxy-3,3'-dicyclohexyl-5,5'-dimethylphenylmethane, 2,2'-methylenebis[6-(1-methylcyclohexyl)-p-cresol], 1,3,5-tris(4-tert-butyl-3-hydroxy-2,6-dimethylbenzyl)isocyanuric acid, 1,3,5-tris(3,5-di-tert-butyl-4-hydroxybenzyl)-s-triazine-2,4,6(1H,3H,5H)-trione, triethyleneglycol bis[3-(3-tert-butyl-4-hydroxy-5-methylphenyl)propionate], 2,2'-oxamide bis[ethyl 3-(3,5-ditert-butyl-4-hydroxyphenyl)propionate], 6-(4-hydroxy-3,5-ditert-butylanilino)-2,4-dioctylthio-1,3,5-triazine, bis[2-tert-butyl-4-methyl-6-(2-hydroxy-3-tert-butyl-5-methyl-benzyl)-phenyl]terephthalate, 3,9-bis[2-[3-(3-tert-butyl-4-hydroxy-5-methylphenyl)propionyloxy]-1,1-dimethylethyl]-2,4,8,10-tetraoxaspiro[5.5]undecane, 3,9-bis[2-[3-(3,5-di-tert-butyl-4-hydroxyphenyl)propionyloxy)-1,1-dimethylethyl]-2,4,8,10-tetraoxaspiro[5.5]undecane, 3,9-bis[2-[3-(3,5-di-tert-butyl-4-hydroxyphenyl)-propionyloxy)-1,1-dimethylethyl]-2,4,8,10-tetraoxaspiro[5.5]-undecane acid and the like, which are not limitative.

When the compounds (I) of the present invention are used as stabilizing agents for organic materials, they are added to the organic materials preferably in a proportion of 0.01 to 5 weight % relative to the organic materials. When at least one of the compounds (I) is used in combination with at least one of hindered phenol compounds as the stabilizing agents, it can be incorporated into organic materials preferably in a proportion of 0.01 to 5 weight % relative to the organic materials, and the ratio of the compound (I) and the hindered phenol compounds may range from 10:1 to 1:5, preferably from 5:1 to 1:2.

The compound (I) of the present invention is singly or in combination with a hindered phenol compound incorporated into organic materials by a method of mixing followed by treatment by processes such as kneading and extrusion.

A thioalkanoate compound selected from the group consisting of dilauryl thiodipropionate, distearyl thiodipropionate, dimyristyl thiodipropionate and pentaerythritol tetrakis($\beta$-laurylthiopropionate) can also be used together with the compounds of the present invention.

When the compound (I) of the present invention is used as stabilizing agents for organic materials, it can be used further in combination with salicylic acid, benzophenone, benzotriazole, cyanoacrylate, piperidine and nickel compoundlight stabilizing agents exemplified by phenyl salicylate, p-tert-butyl salicylate, p-octylphenyl salicylate, 2,4-dihydroxybenzophenone, 2-hydroxy-4-acetoxyethoxybenzophenone, 2-hydroxy-4-methoxybenzophenone, 2,2'-dihydroxy-4,4'-methoxybenzophenone, 2-hydroxy-4-n-octyloxybenzophenone, 2-hydroxy-4-isooctyloxybenzophenone, 2-hydroxy-4-dodecyloxybenzophenone, di-sodium 2-hydroxy-4-octadecyloxybenzophenone, 2,2'-dihydroxy-4,4'-dimethoxy-5,5'-disulfobenzophenone, 2-hydroxy-4-(2-hydroxy-3-methacryloxy)propoxybenzophenone, 2-(2-hydroxy-5-methylphenyl)-benzotriazole, 2-(2-hydroxy-3,5-di-tert-butylphenyl)benzotriazole, 2-(2-hydroxy-3-tert-butyl-5-methylphenyl)-5-chlorobenzotriazole, 2-(2-hydroxy-3,5-di-tert-butylphenyl)-5-chlorobenzotriazole, 2-(2-hydroxy-3,5-di-tert-butylphenyl)benzotriazole, 2-(2-hydroxy-5-tert-octylphenyl)benzotriazole, 2,4-di-tert-butylphenyl 3,5-di-tert-butyl-4-hydroxybenzoate, ethyl 2-cyano-3,5-diphenylacrylate, nickel[2,2-thiobis(4-tert-octylphenolate)]-n-butylamine, nickel bis(octylphenylsulfide), nickel bis[o-ethyl(3,5-di-tert-butyl-4-hydroxybenzyl)]phosphonate, bis(2,2,6,6-tetramethyl-4-piperidine)sebacate, bis(1,2,2,6,6-pentamethyl-4-piperidyl)-n-butyl-3,5-di-tert-butyl-4-hydroxybenzylmalonate, tetrakis(2,2,6,6-tetramethyl-4-piperidyl)butane-1,2,3,4-tetracarboxylate, poly{[6-(1,1,3,3-tetramethyl- 4-piperidyl)amino]-s-triazine-2,4-diyl}, [(2,2,6,6-tetramethyl-4-piperidyl)imino]hexamethylene[(2,2,6,6-tetramethyl-4-piperidyl)imino], poly(6-morpholino-s-triazine-2,4-diyl)[(2,2,6,6-tetramethyl-4-piperidyl)imino]hexamethylene-[(2,2,6,6-tetramethyl-4-piperidyl)imino], 1-hydroxyethyl-2,2,6,6-tetramethyl-4-piperidinol/succinic acid condensate, cyanulic chloride/tert-octylamine/1,6-bis(2,2,6,6-tetramethyl-4-piperidylamino)hexane condensate, or metal soaps, heavy metal inactivating agents, nucleator, organic tin compounds, plasticizers, epoxy compounds, pigments, fillers, a foaming agents, anti-electrifying agents, flame-retardants, lubricants, process auxiliaries and the like.

Hitherafter, the antioxidant effects of the compounds of the present invention are shown by the experimental examples.

EXPERIMENTAL EXAMPLE 1

To polypropylene powders 98% of which are isotactic ones having an intrinsic viscosity of 1.9 when measured in tetralin at 135° C. was added an antioxidant, and the mixture was well mixed in a mixer. The mixture was melted and kneaded with the extruder of a diameter of 20 mm with a ratio of L/D of 20 at a cylinder temperature of 260° C. to be granulated. The MFR (JIS K6758) at 230° C. of the thus obtained pellets was measured and taken as $MFR_1$. Further, the mixture was subjected to the extruder three times repeatedly under the abovementioned conditions as regards kneading and granulation. The MFR at 230° C. of the thus obtained pellets was taken as $MFR_4$.

MFR is one of indexes for molecular weight. The higher MFR is, the smaller the molecular weight is. That is, if $MFR_1$ and $MFR_4$ are lower and the balance of $MFR_1$ and $MFR_4$ is small, it is meant that small is the decrease in molecular weight owing to oxidation and deterioration in the extruder. When the antidoxidants are used, it is meant that the antioxidant effects thereof are great.

|   | Antioxidant | $MFR_1$ | $MFR_4$ |
|---|---|---|---|
| Comparative example | none | 12.3 | not less than 50 |
| Comparative example | 3,9-Bis(octadecyloxy)-2,4,8,10-tetraoxa-3,9-phosphaspiro[5.5]undecane 0.1PHR | 8.5 | 40 |
| Example of the present invention | Tris[2-tert-butyl-4-(2-octadecyloxycarbonyl)-ethylphenyl]phosphite 0.1PHR | 7.0 | 27 |
| Comparative example | Tetrakis[3-(3,5-di-tert-butyl-4-hydroxyphenyl)propionyloxymethyl]methane 0.1PHR 3,9-Bis(octadexyloxy)-2,4,8,10-tetraoxa-3,9-phosphaspiro[5.5]undecane 0.1PHR | 5.2 | 11.7 |
| Example of the present invention | Tetrakis[3-(3,5-di-tert-butyl-4-hydroxyphenyl)-propionyloxymethyl]methane 0.1PHR | 3.5 | 4.2 |
| Application example | Tris[2-tert-butyl-4-(2-(octadecyloxycarbonyl)ethyl)phenyl]phosphite 0.1PHR |   |   |

EXPERIMENTAL EXAMPLE 2

Representative phosphite compounds hitherto known and the compounds (I) of the present invention are examined for their heat resistance, and the results were shown in FIG. 1 for the comparison of their heat resistance.

In FIG. 1, the compounds a, b and c mean the following compounds respectively.

Compound a: Tris(2,4-di-tert-butylphenyl)phosphite(hithertoknown compound)

Compound b: 3,9-Bis(octadecyloxy)-2,4,8,10-tetraoxa-3,9-phosphaspiro[5,5]undecane (hitherto-known compound)

Compound c: Tris[2-tert-butyl-4-(2-(octadecyloxycarbonyl)ethyl) phenyl]phosphite [The compound (I) of this invention]

The equipment used for this experiment was Thermofrec 8100 type manufactured by Rigaku. The behaviors in weightdecrease of the compounds were measured.

Below, the present invention is in detail explained by reference examples and working examples, which are not to be construed as limitative. The obtained compounds were ascertained respectively as the objective compounds (I) by such means as infrared absorption spectrum, nuclear magnetic resonance spectrum, mass spectrum and elemental analysis.

REFERENCE EXAMPLE (Production Example of Starting Compounds)

(1) A mixture of 45 g of methyl 3-(3-tert-butyl-4-hydroxyphenyl)propionate, 24.7 g of 2-ethylhexylalcohol, 0.5 g of dibutyltin oxide and 50 ml of toluene was heated to 140° C., whereto toluene was further added while the solvent was being distilled off. After the mixture was stirred for 10 hours, toluene was distilled off. The obtained residue was purified by silica gel column chromatography to give 60 g of 2-ethylhexyl 3-(3-tert-butyl-4-hydroxyphenyl)propionate as a pale yellow oily substance.

By using dodecyl alcohol, tridecyl alcohol, octadecyl alcohol, dococyl alcohol or benzyl alcohol instead of 2-ethylhexyl alcohol, the same reaction and treatment as the above-mentioned was conducted to give the following compounds.

Dodecyl 3-(3-tert-butyl-4-hydroxyphenyl)propionate as a pale yellow oily substance;

Tridecyl 3-(3-tert-butyl-4-hydroxyphenyl)propionate as a pale yellow oily substance;

Octadecyl 3-(3-tert-butyl-4-hydroxyphenyl)propionate as a white crystal, m.p. 43°–45° C.;

Dococyl 3-(3-tert-butyl-4-hydroxyphenyl)propionate as a white crystal, m.p. 44°–47° C.;

Benzyl 3-(3-tert-butyl-4-hydroxyphenyl)propionate as a pale yellow oily substance;

(2) A mixture of 55 g of 3-(3-tert-butyl-4-hydroxyphenyl)-propionic acid, 35 g of phenol, 7 g of dimethylformamide, 19.1 g of phosphorus oxychloride and 250 ml of toluene was stirred at 70° C. for 6 hours. The mixture was cooled to room temperature, and 800 ml of toluene was added thereto. The mixture was washed with water and an aqueous solution of sodium hydroxide, followed by washing with water. The mixture was concentrated, and the residue was purified by silica gel column chromatography to give 66.5 g of phenyl 3-(3-tert-butyl-4-hydroxyphenyl)propionate as a white crystal, m.p. 106°–109° C.

By using 3-methylphenol, 4-tert-butylphenol or 2,6-dimethylphenol instead of phenol, the same reaction and treatment as mentioned above was conducted to give the following compounds.

3-Methylphenyl 3-(3-tert-butyl-4-hydroxyphenyl)propionate as a white crystal, m.p. 96°–98° C.

4-Tert-butylphenyl 3-(3-tertbutyl-4-hydroxyphenyl)propionate as a white crystal, m.p. 104°–106° C.

2,6-Dimethylphenyl 3-(3-tert-butyl-4-hydroxyphenyl)propionate as a white crystal, m.p. 101°–104° C.

(3) A mixture of 50 g of methyl 3-(3,5-di-tert-butyl-4-hydroxyphenyl)propionate, 2.5 g of conc. hydrochloric acid and 30 ml of toluene was refluxed for 2 hours while stirring. After the completion of the reaction, the reaction mixture was washed with water and the solvent wa distilled off. Hexane was added to the residue and the mixture was icecooled. The resulting crystals were collected by filtration and recrystallized from hexane to give 29 g of methyl 3-(3-tert-butyl-4-hydroxyphenyl)propionate as white crystals, m.p. 59°–61° C.

EXAMPLE 1

To a solution of 23.6 g of methyl 3-(3-tert-butyl-4-hydroxyphenyl)propionate, 0.47 g of pyridine and 60 ml of toluene was added dropwise 4.5 g of phosphorus trichloride at 70° C., and the mixture was heated, and refluxed while stirring for 6 hours. After the completion of the reaction, the reaction mixture was cooled to room temperature. Thereto were added 30 ml of water and 40 ml of toluene, and the mixture was washed with water. The mixture was subjected to separation. The toluene layer was concentrated and purified by silica gel column chromatography to give 63 g of tris[2-tert-butyl-4-(2-(methoxycarbonyl)ethyl)phenyl]phosphite as a pale yellow oily substance.

| Elemental Analysis | C (%) | H (%) | P (%) |
|---|---|---|---|
| Calcd. | 68.45, | 7.79, | 4.2 |
| Found | 68.55, | 7.73, | 4.15 |

IR (cm$^{-1}$): $\gamma_{P-O}$ 850, 1190; $\gamma_{C=O}$ 17.35 (Film).

NMR (CDCl$_3$): δ 1.20–1.40 (m, 27H), 2.50–3.0 (m, 12H), 3.63 (s, 9H), 6.80–7.30 (m, 9H).

EXAMPLES 2-9

By using the corresponding 2-ethylhexyl ester, tridecyl ester, octadecyl ester, dococyl ester, benzyl ester, phenyl ester, 3-methylphenyl ester or 2,6-dimethylphenyl ester instead of methyl 3-(3-tert-butyl-4-hydroxyphenyl)propionate, the reactions and treatments were conducted in the same manner as in Example 1 to give the following compounds.

Tris[2-tert-butyl-4-(2-(2-ethylhexyloxycarbonyl)ethyl)-phenyl]phosphite as a pale yellow oily substance

| Elemental Analysis | C (%) | H (%) | P (%) |
|---|---|---|---|
| Calcd. | 73.36, | 9.67, | 3.0 |
| Found | 73.11, | 9.73, | 3.06 |

IR (cm$^{-1}$): $\gamma_{P-O}$ 845, 1180; $\gamma_{C=O}$ 1730 (Film).

NMR (CDCl$_3$): δ 0.60–1.70 (m, 72H), 2.50–3.0 (m, 12H), 4.0 (d, 6H), 6.80–7.30 (m, 9H).

Tris[2-tert-butyl-4-(2-(tridecyloxycarbonyl)ethyl)-phenyl]-phosphite as a pale yellow oily substance

| Elemental Analysis | C (%) | H (%) | P (%) |
|---|---|---|---|
| Calcd. | 75.44, | 10.46, | 2.49 |

-continued

| Elemental Analysis | C (%) | H (%) | P (%) |
| --- | --- | --- | --- |
| Found | 75.57, | 10.40, | 2.40 |

IR (cm⁻¹): $\gamma_{P\text{-}O}$ 845, 1185; $\gamma_{C=O}$ 1730 (Film).
NMR (CDCl₃): δ 0.60–1.70 (m, 102H), 2.40–3.0 (m, 12H), 4.0 (t, 6H), 6.80–7.30 (m, 9H).

Tris[2-tert-butyl-4-(2-(octadecyloxycarbonyl)ethyl)-phenyl]-phosphite as white crystals, m.p. 35°–37° C.

| Elemental Analysis | C (%) | H (%) | P (%) |
| --- | --- | --- | --- |
| Calcd. | 76.91, | 11.03, | 2.13 |
| Found | 77.04, | 11.07, | 2.19 |

IR (cm⁻¹): $\gamma_{P\text{-}O}$ 845, 1185; $\gamma_{C=O}$ 1735 (Film).
NMR (CDCl₃): δ 0.60–1.80 (m, 132H), 2.40–3.0 (m, 12H), 4.02 (t, 6H), 6.80–7.30 (m, 9H).

Tris[2-tert-butyl-4-(2-(dococyloxycarbonyl)ethyl)-phenyl]-phosphite as white crystals, m.p. 39°–40° C.

| Elemental Analysis | C (%) | H (%) | P (%) |
| --- | --- | --- | --- |
| Calcd. | 77.82, | 11.38, | 1.91 |
| Found | 78.01, | 11.30, | 1.87 |

IR (cm⁻¹): $\gamma_{P\text{-}O}$ 845, 1185; $\gamma_{C=O}$ 1735 (Film).
NMR (CDCl₃): δ 0.60–1.85 (m, 156H), 2.40–3.0 (m, 12H), 4.0 (t, 6H), 6.80–7.30 (m, 9H).

Tris[2-tert-butyl-4-(2-(benzyloxycarbonyl)ethyl)-phenyl]-phosphite as a yellow oily substance

| Elemental Analysis | C (%) | H (%) | P (%) |
| --- | --- | --- | --- |
| Calcd. | 74.66, | 7.2, | 3.2 |
| Found | 74.80, | 7.35, | 3.13 |

IR (cm⁻¹): $\gamma_{P\text{-}O}$ 850, 1185; $\gamma_{C=O}$ 1735 (Film).
NMR (CDCl₃): δ 1.20–1.50 (m, 27H), 2.50–3.05 (m, 12H), 5.05 (s, 6H), 6.80–7.50 (m, 24H).

Tris[2-tert-butyl-4-(2-(phenoxycarbonyl)ethyl)-phenyl]-phosphite as a pale yellow oily substance

| Elemental Analysis | C (%) | H (%) | P (%) |
| --- | --- | --- | --- |
| Calcd. | 74.16, | 6.87, | 3.35 |
| Found | 74.45, | 6.80, | 3.31 |

IR (cm⁻¹): $\gamma_{P\text{-}O}$ 845, 1190; $\gamma_{C=O}$ 1755 (Film).
NMR (CDCl₃): δ 1.38 (s, 27H), 2.60–3.10 (m, 12H), 6.80–7.40 (m, 24H).

Tris[2-tert-butyl-4-(2-(3-methylphenoxycarbonyl)ethyl)-phenyl]phosphite as a pale yellow oily substance

| Elemental Analysis | C (%) | H (%) | P (%) |
| --- | --- | --- | --- |
| Calcd. | 74.66, | 7.2, | 3.2 |
| Found | 74.32, | 7.31, | 3.30 |

IR (cm⁻¹): $\gamma_{P\text{-}O}$ 850, 1190; $\gamma_{C=O}$ 1755 (Film).
NMR (CDCl₃): δ 1.38 (s, 27H), 1.33 (s, 9H), 2.60–3.10 (m, 12H), 6.50–7.40 (m, 21H).

Tris[2-tert-butyl-4-(2-(2,6-dimethylphenoxycarbonyl)ethyl)phenyl]phosphite as a pale yellow substance

| Elemental Analysis | C (%) | H (%) | P (%) |
| --- | --- | --- | --- |
| Calcd. | 75.12, | 7.5, | 3.07 |
| Found | 75.39, | 7.29, | 2.99 |

IR (cm⁻¹): $\gamma_{P\text{-}O}$ 845, 1190; $\gamma_{C=O}$ 1750 (Film).
NMR (CDCl₃): δ 1.40 (s, 27H), 2.40 (s, 18H), 2.70–3.15 (m, 12H), 6.70–7.40 (m, 18H).

EXAMPLE 10

A mixture of 11.7 g of dodecyl 3-(3-tert-butyl-4-hydroxyphenyl)propionate, 3.1 g of triphenylphosphite and a slight amount of sodium hydroxide was stirred at 150°–200° C. After the elimination of phenol, the mixture was cooled to room temperature and purified by silica gel column chromatography to give tris[2-tert-butyl-4-(2-(dodecyloxycarbonyl)ethyl)-phenyl]phosphite as a pale yellow oily substance.

| Elemental Analysis | C (%) | H (%) | P (%) |
| --- | --- | --- | --- |
| Calcd. | 75.08, | 10.33, | 2.58 |
| Found | 74.90, | 10.21, | 2.63 |

IR (cm⁻¹): $\gamma_{P\text{-}O}$ 845, 1185; $\gamma_{C=O}$ 1735 (Film).
NMR (CDCl₃): δ 0.60–1.70 (m, 96H), 2.40–3.0 (m, 12H), 4.0 (t, 6H), 6.80–7.30 (m, 9H).

EXAMPLE 11

By using 4-tert-butylphenyl 3-(3-tert-butyl-4-hydroxyphenyl)propionate and tributylphosphite, the reactions and treatments were conducted in the same manner as in Example 10 to give tris[2-tert-butyl-4-(2-(4-tert-butylphenoxycarbonyl)-ethyl)phenyl]phosphite.

| Elemental Analysis | C (%) | H (%) | P (%) |
| --- | --- | --- | --- |
| Calcd. | 75.93, | 8.03, | 2.83 |
| Found | 76.10, | 8.00, | 2.98 |

IR (cm⁻¹): $\gamma_{P\text{-}O}$ 850, 1130; $\gamma_{C=O}$ 1755 (Film).
NMR (CDCl₃): δ 1.31 (s, 27H), 1.38 (s, 27H), 2.60–3.10 (m, 12H), 6.70–7.40 (m, 21H).

The present invention has been fully explained in the description and examples given above, but any variations and modifications thereof may be made without departing from the spirit and scope of the present invention.

We claim:

1. A phosphite compound represented by the formula

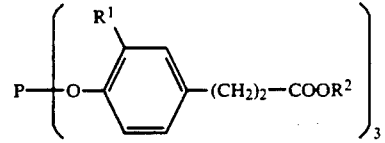

wherein R¹ stands for a tertiary butyl group, R² stands for a straight- or branched-alkyl group having 1 to 22 carbon atoms; or phenyl group.

2. The phosphite compound according to claim 1 selected from the group consisting of tris[2-tert-butyl-4-(2-(methoxycarbonyl)ethyl)phenyl]phosphite, tris[2-tert-butyl-4-(2-(2-ethylhexyloxycarbonyl)ethyl)-phenyl]phosphite, tris[2-tert-butyl-4-(2-(tridecyloxycarbonyl)ethyl)phenyl]phosphite, tris[2-tert-butyl-4-(2-(octadecyloxycarbonyl)ethyl)phenyl]phosphite, tris[2-tert-butyl-4-(2-(2-(dococyloxycarbonyl)ethyl)-phenyl]phosphite, tris[2-tert-butyl-4-(2-(phenoxycarbonyl)ethyl)phosphite, and tris[2-tert-butyl-4-(2-(dodecyloxycarbonyl)ethyl)-phenyl]]phosphite.

* * * * *